(12) United States Patent
Chapeau et al.

(10) Patent No.: US 8,012,433 B2
(45) Date of Patent: Sep. 6, 2011

(54) DEVICE FOR DISPERSING DRY POWDERS

(75) Inventors: Vincent Chapeau, Seraing (BE);
Christian Godino, Liege (BE)

(73) Assignee: Occhio Parc Scientifique Du Sart Tilman, Liege (Angleur) (BE)

( * ) Notice: Subject to any disclaimer, the term of this patent is extended or adjusted under 35 U.S.C. 154(b) by 0 days.

(21) Appl. No.: 12/975,113

(22) Filed: Dec. 21, 2010

(65) Prior Publication Data

US 2011/0120368 A1  May 26, 2011

Related U.S. Application Data

(63) Continuation of application No. 11/570,161, filed on Dec. 7, 2006, now Pat. No. 7,883,902.

(30) Foreign Application Priority Data

Jun. 8, 2004 (BE) .................................. 2004/282

(51) Int. Cl.
*B01L 3/14* (2006.01)

(52) U.S. Cl. .......... 422/550; 422/63; 422/500; 422/547; 422/570; 436/56; 436/174; 118/50; 118/309

(58) Field of Classification Search ............. 422/63, 422/500, 547, 550, 570; 436/56, 174; 118/50, 118/309
See application file for complete search history.

(56) References Cited

U.S. PATENT DOCUMENTS

| | | | |
|---|---|---|---|
| 2,153,419 A * | 4/1939 | Hoffman | 222/4 |
| 2,210,470 A * | 8/1940 | Sterling | 222/637 |
| 2,758,564 A * | 8/1956 | Randall | 118/309 |
| 2,993,469 A * | 7/1961 | Tarpley Jr., et al. | 118/303 |
| 3,472,202 A * | 10/1969 | Webb | 118/308 |
| 3,537,426 A * | 11/1970 | Smith et al. | 118/629 |
| 3,663,788 A * | 5/1972 | Inoue | 219/76.13 |
| 3,854,321 A * | 12/1974 | Dahneke | 73/28.01 |
| 3,903,838 A * | 9/1975 | Bennett et al. | 118/308 |
| 3,938,469 A * | 2/1976 | Nau | 118/303 |
| 3,949,751 A * | 4/1976 | Birch et al. | 128/203.15 |
| 4,089,989 A * | 5/1978 | White et al. | 427/2.11 |
| 4,134,512 A * | 1/1979 | Nugent | 215/247 |
| 4,344,573 A * | 8/1982 | De Felice | 239/320 |
| 4,764,057 A * | 8/1988 | Molter et al. | 406/69 |
| 4,868,128 A * | 9/1989 | Sommer et al. | 436/174 |

(Continued)

FOREIGN PATENT DOCUMENTS

JP         2001242062 A  *  9/2001

(Continued)

*Primary Examiner* — In Suk Bullock
*Assistant Examiner* — Dennis M White
(74) *Attorney, Agent, or Firm* — McCracken & Frank LLP

(57) ABSTRACT

A device for dispersing a sample of dry powder onto a surface in a dispersion chamber. The device includes a dispersion chamber situated in an environment, and a pressure source that provides a pressure difference between the environment and an inside of the dispersion chamber. The surface is positioned in the dispersion chamber. The sample of dry powder is introduced into the dispersion chamber through a membrane that is interposed between the environment and the inside of the dispersion chamber and on which the sample is disposed. The membrane is rupturable so as to open into the dispersion chamber when a predetermined pressure difference across the membrane is exceeded. This permits entry of a fluid in the environment through the ruptured membrane, and movement of the dry powder sample in an evenly dispersed manner without producing an ordered movement of powder grains in the dispersion chamber.

6 Claims, 1 Drawing Sheet

U.S. PATENT DOCUMENTS

Figure 1:
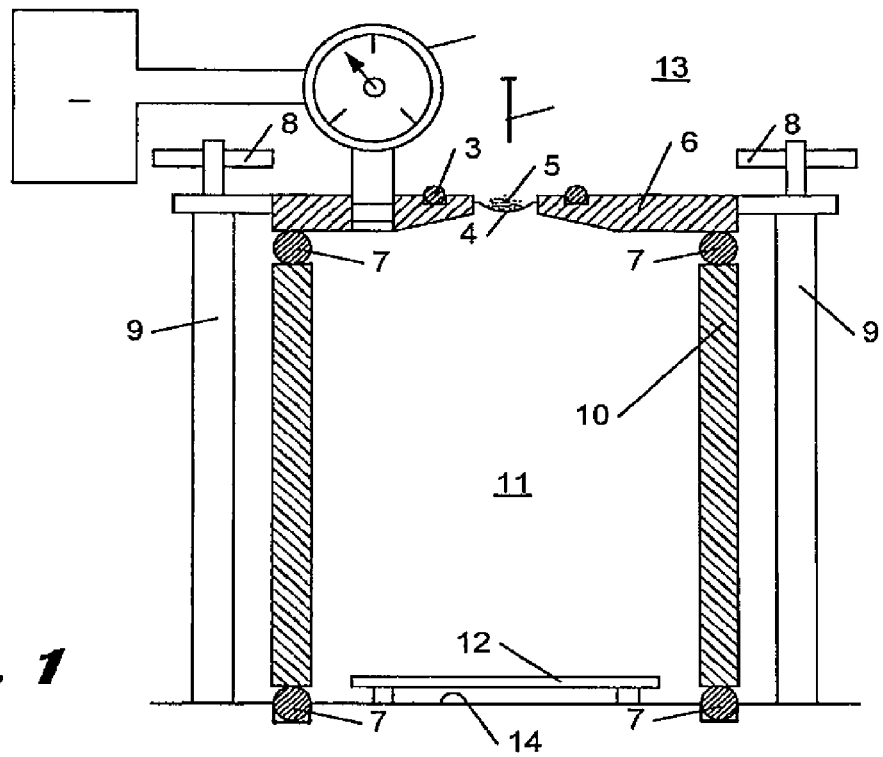
Figure 2:
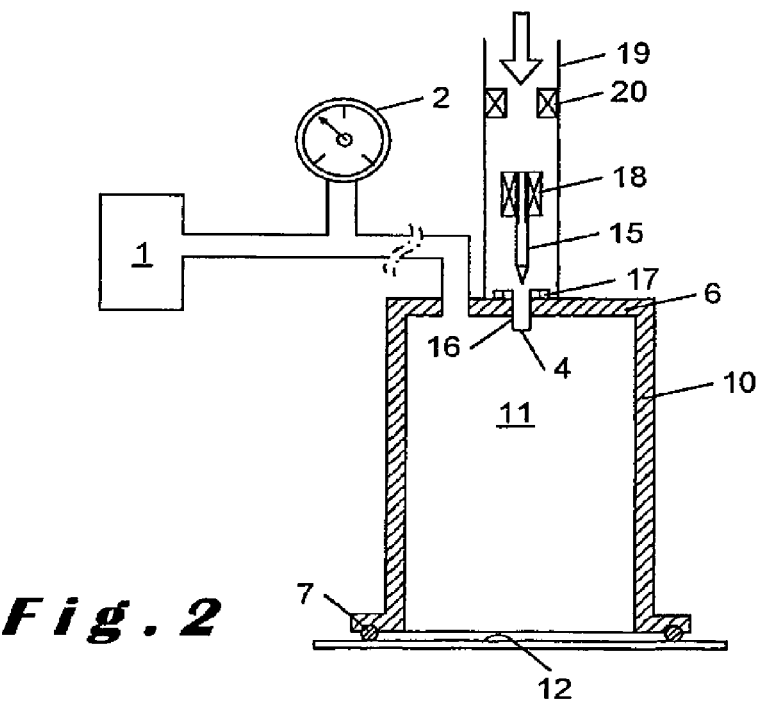

| | | | | |
|---|---|---|---|---|
| 5,349,947 A * | 9/1994 | Newhouse et al. | ...... | 128/203.21 |
| 5,463,524 A * | 10/1995 | Szirmai | ......... | 361/230 |
| 5,474,059 A * | 12/1995 | Cooper | ......... | 128/200.22 |
| 5,507,602 A * | 4/1996 | Walker | ......... | 406/122 |
| 5,522,555 A * | 6/1996 | Poole | ......... | 241/33 |
| 5,694,920 A * | 12/1997 | Abrams et al. | ......... | 128/200.16 |
| 5,785,049 A * | 7/1998 | Smith et al. | ......... | 128/203.15 |
| 5,800,876 A * | 9/1998 | Borner et al. | ......... | 427/459 |
| 5,875,776 A * | 3/1999 | Vaghefi | ......... | 128/203.15 |
| 5,881,719 A * | 3/1999 | Gottenauer et al. | ..... | 128/203.15 |
| 5,941,867 A * | 8/1999 | Kao | ......... | 604/416 |
| 5,956,413 A * | 9/1999 | Oste et al. | ......... | 382/110 |
| 6,029,662 A * | 2/2000 | Marcon | ......... | 128/203.15 |
| 6,123,070 A * | 9/2000 | Bruna et al. | ......... | 128/203.15 |
| 6,179,164 B1 * | 1/2001 | Fuchs | ......... | 222/82 |
| 6,209,538 B1 * | 4/2001 | Casper et al. | ......... | 128/203.15 |
| 6,257,233 B1 * | 7/2001 | Burr et al. | ......... | 128/203.15 |
| 6,332,461 B1 * | 12/2001 | Hyppola | ......... | 128/203.15 |
| 6,443,152 B1 * | 9/2002 | Lockhart et al. | ......... | 128/203.21 |
| 6,591,832 B1 * | 7/2003 | DeJonge | ......... | 128/203.14 |
| 6,606,992 B1 * | 8/2003 | Smith et al. | ......... | 128/203.15 |
| 6,701,922 B2 * | 3/2004 | Hindle et al. | ......... | 128/203.27 |
| 6,779,520 B2 * | 8/2004 | Genova et al. | ......... | 128/200.22 |
| 7,518,716 B2 * | 4/2009 | Canty et al. | ......... | 356/237.1 |
| 7,530,197 B2 * | 5/2009 | Timmis et al. | ......... | 47/57.6 |
| 2002/0078883 A1 * | 6/2002 | Shutic et al. | ......... | 118/50 |
| 2002/0127701 A1 * | 9/2002 | Duncan | ......... | 435/245 |
| 2005/0004502 A1 * | 1/2005 | O'Mahony et al. | ......... | 604/4.01 |
| 2005/0016533 A1 * | 1/2005 | Schuler et al. | ......... | 128/203.15 |
| 2007/0107721 A1 * | 5/2007 | Olsson et al. | ......... | 128/200.23 |
| 2007/0116752 A1 * | 5/2007 | Chowdhury | ......... | 424/449 |
| 2007/0119450 A1 * | 5/2007 | Wharton et al. | ......... | 128/200.23 |
| 2008/0261325 A1 * | 10/2008 | Chapeau et al. | ......... | 436/174 |

FOREIGN PATENT DOCUMENTS

WO     WO 03/074154 A1 *    9/2003

* cited by examiner

DEVICE FOR DISPERSING DRY POWDERS

This is a continuation of U.S. patent application Ser. No. 11/570,161, filed Dec. 7, 2006, which claims priority to PCT/EP2005/052612, filed Jun. 7, 2005, and also claims the benefit of foreign priority to BE 2004-282, filed Jun. 8, 2004, which is hereby incorporated herein by reference in its entirety.

BACKGROUND OF THE INVENTION

1. Field of the Invention

The present invention relates to a method and device for dispersing a sample of dry powder in a dispersion chamber.

2. Description of Prior Art

There is known, for example through the U.S. Pat. No. 4,868,128, a method of dispersing a sample of dry powder in a dispersion chamber comprising:
sealed closure of the said dispersion chamber,
the placing of the sample in means of introducing dry powder into the dispersion chamber,
putting the chamber under negative pressure with respect to a surrounding environment,
dispersion of the dry powder in the chamber by suction thereof inside.

In addition, the device described in the above mentioned patent comprises:
a dispersion chamber connected to a negative-pressure source and situated in a surrounding environment,
means of opening and/or sealed closure of the said dispersion chamber, and
means of introducing the sample of dry powder into the said dispersion chamber.

Unfortunately, this method and this device cause an ordered dispersion of the grains constituting the dry powder because of the existence of a flow and this involves segregation within the dispersed granular materials, preventing a certain homogeneity of dispersion of the grains on a surface.

SUMMARY OF THE INVENTION

The aim of the invention is to mitigate the drawbacks of the prior art by procuring an invention making it possible to avoid this segregation and permitting homogeneous, preferably single-layer, distribution of the grains dispersed on the surface.

To resolve this problem, there is provided according to the invention a method as indicated at the start, also comprising

- explosion of a membrane that ruptures, this membrane serving as the above mentioned introduction means and being interposed between the said surrounding environment and the interior of the said dispersion chamber,
- entry of a fluid composing the surrounding environment through the ruptured membrane, and
- entrainment by this fluid of the dry powder placed on the membrane, inside the dispersion chamber in an evenly dispersed manner.

Other embodiments of the method according to the invention are indicated in the accompanying claims.

Another object of the invention is a device as indicated at the start for implementing the method described above.

This device is characterised in that the introduction means comprise a membrane that is interposed between the said surrounding environment and the inside of the said dispersion chamber and on which the sample is disposed, the said membrane being arranged to rupture at a predetermined pressure difference between the said surrounding environment and the said inside of the dispersion chamber.

Other embodiments of the device according to the invention are indicated in the accompanying claims.

Other characteristics, details and advantages of the invention will emerge from the description given below, non-limitingly and making reference to the accompanying drawing.

BRIEF DESCRIPTION OF THE DRAWINGS

FIG. 1 is a schematic view of a particular embodiment of the device according to the invention.

FIG. 2 is a schematic view of a variant embodiment of the device according to the invention.

DETAILED DESCRIPTION OF THE DRAWINGS

FIG. 1 illustrates a particular embodiment of the device comprising a vacuum pump 1, a pressure gauge 2, means of introducing a sample into the dispersion chamber 11, in the form of a sample support membrane 4, on which provision is made for disposing a sample of dry powder 5, and a surface (surface to be treated 12) on which the sample of dry powder is to be dispersed. The dispersion chamber 11 consists of a cylinder 10, a top cover 6 and a bottom 14. These elements 10, 6 and 14 can be assembled in order to form a dispersion chamber. On the bottom 14, a seal 7 is placed on which the cylinder 10 must be placed for assembly. Above the cylinder 10, provision is made for placing another seal 7 before closing the dispersion chamber by means of the cover 6. In addition, clamping means, for example of the type with closure column 9 and butterflies 8, ensure a seal by pushing the cover 6 and bottom 1 onto the seals on each side of the cylinder 11. The clamping means 8 and 9 and sealing means 7 therefore form the opening and/or sealed closure means of the device according to the invention. In addition, when the partial vacuum is produced, the cover 6 and bottom 14 exert an even greater pressure on the seals. The cover 6 and bottom 14 therefore grip the cylinder 10 sealingly.

The device that is described above is an apparatus for dispersing a sample of dry powder 5 by explosion in a vacuum dispersion chamber 11. This technique allows the dispersion of micrometric or nanometric grains of dry powder 5 on a surface positioned in the bottom of the dispersion chamber 11, the surface to be treated 12.

This dispersion is carried out by separating and setting in movement the sample of dry powder 5 without producing an ordered movement of the grains making up the dry powder 5, in the dispersion chamber 11. This condition of not generating an ordered movement of the material (a flow) is essential since a flow generates segregation within the dispersed granular materials, which is very detrimental in the context of the subsequent analyses.

In order to perform the dispersion operation, a low-intensity explosion is generated. This explosion is generated by the rupture of the sample-holding membrane 4, the membrane 4 being interposed between a surrounding environment 13 and the dispersion chamber 11 in which an at least partial vacuum was previously established.

The non-ordered movement of the sample of dry powder 5 is effected by a turbulent filling of the dispersion chamber 11 with ambient air 13 or any gas. This gas or the ambient air 13 is then used as a carrier of the material within the dispersion chamber 11.

This explosion and the filling of the dispersion chamber 11 with ambient air 13 or any gas gives rise to an unexpected phenomenon. The grains making up the sample of dry powder 5 have a tendency to push against one another and to form an homogeneous cloud of material within the dispersion chamber 11.

The sample of dry powder 5 is recovered for the purpose of analysis by a process of natural sedimentation of the grains in the dispersion chamber 11 on the surface to be treated 12.

In addition, when the surrounding pressure in the dispersion chamber is re-established owing to the rupture of the membrane 4, the butterflies prevent a lifting of the cylinder 10 and maintain the seal in order to prevent a loss of sample 4.

In order to use the device illustrated in FIG. 1, it is possible to proceed in the following manner. The sur